United States Patent [19]

Moro et al.

[11] Patent Number: 4,460,577
[45] Date of Patent: Jul. 17, 1984

[54] PHARMACEUTICAL COMPOSITIONS CONSISTING OR CONSISTING ESSENTIALLY OF LIPOSOMES, AND PROCESSES FOR MAKING SAME

[75] Inventors: Luigi Moro, Cairate; Guido Neri; Alessandro Rigamonti, both of Milan, all of Italy

[73] Assignee: Farmitalia Carlo Erba S.p.A., Milan, Italy

[21] Appl. No.: 111,837

[22] Filed: Jan. 14, 1980

Related U.S. Application Data

[63] Continuation-in-part of Ser. No. 945,515, Sep. 25, 1978, abandoned.

[30] Foreign Application Priority Data

Sep. 30, 1977 [IT] Italy ................... 28147 A/77
Jan. 19, 1979 [IT] Italy ................... 19434 A/79

[51] Int. Cl.$^3$ ............. A61K 31/70; A61K 31/74; A61K 31/505
[52] U.S. Cl. .................. 424/180; 424/79; 424/251
[58] Field of Search ......... 424/36, 38, 79, 180, 424/251, 365; 252/316, 82, 83; 210/502, 660, 927

[56] References Cited

U.S. PATENT DOCUMENTS

| | | | |
|---|---|---|---|
| 3,398,092 | 8/1968 | Fields | 424/79 |
| 3,794,584 | 2/1974 | Kunin | 424/79 |
| 3,887,698 | 6/1975 | McConnell | 424/12 |
| 3,993,754 | 11/1976 | Rahman | 424/177 |
| 4,016,100 | 4/1977 | Suzaki | 424/36 |
| 4,131,544 | 12/1978 | Elahi | 23/230 B |
| 4,145,304 | 3/1979 | Melnick | 424/79 |
| 4,229,360 | 10/1980 | Schneider | 424/36 |
| 4,298,594 | 11/1981 | Sears | 424/38 |

FOREIGN PATENT DOCUMENTS

2249552 10/1972 Fed. Rep. of Germany ........ 424/14
51-26213 3/1976 Japan ........................ 424/19

OTHER PUBLICATIONS

Tyrrell, Biochem. & Biophys. Acta, vol. 457, 1976, pp. 259-274.
Tritton, Biochem. & Biophys. Res. Comm., vol. 84, 1978, pp. 802-808.
Merck Index, 9th Ed., 1976, No. 3428.
Segal, Clin. Sci. & Molecular Med., vol. 49, 1975, pp. 99-106.

*Primary Examiner*—Albert T. Meyers
*Assistant Examiner*—John W. Rollins, Jr.
*Attorney, Agent, or Firm*—Stevens, Davis, Miller & Mosher

[57] ABSTRACT

A method is disclosed for purifying non-homogeneous systems, known as liposomic suspensions, from non-entrapped drugs wherein said suspensions are treated with liquid or solid polymers of synthetic and organic nature having chemical functionality, which are used as ion-exchangers. The liquid or solid polymers are based on styrene, divinylbenzene, acrylic acid, methacrylic acid, and the like, normally known as ion-exchange resins, and may include carboxylic, phosphonic, or sulphonic functions of different matrices. The ion-exchange resins may also include salified quaternary ammonium, primary, secondary and tertiary amminic or phosphinic functions or other functions with different matrices, including phenolformaldehyde, styrene-divinylbenzene, acrylates, methacrylates, hydrocarbons and condensation-resins. Treatment may also be carried out with polymers, copolymers, or mixtures thereof, not having any specific chemical function and which normally, but not exclusively, react according to Van der Waals' forces, commonly known as adsorbents. The invention also includes pharmaceutical compositions consisting or consisting essentially of lyophilic liposomes of doxorubicin hydrochloride, aminosidine sulphate or 5-fluoro-uracil.

12 Claims, No Drawings

PHARMACEUTICAL COMPOSITIONS CONSISTING OR CONSISTING ESSENTIALLY OF LIPOSOMES, AND PROCESSES FOR MAKING SAME

This application is a continuation-in-part of our copending application Ser. No. 945,515, filed on Sept. 25, 1978, now abandoned.

The present invention relates to pharmaceutical compositions (lyophilic liposomes) and to processes for their preparation and purification.

More particularly, the invention refers to a new method for purifying liposomic suspensions obtained according to per se known methods and for stabilizing same by lyophilization.

Liposomes are pharmaceutical compositions in which the drug is contained either dispersed or variously present in corpuscles consisting of aqueous concentric layers adherent to lipidic layers (hydrophobic). The drug may be present both in the aqueous layer and in the lipidic one (inside or outside) or, in any event, in the non-homogeneous system generally known as a liposomic suspension.

The hydrophobic layer, generally but not exclusively, comprises phospholipids such as lecithin and sphingomycelin, steroids such as cholesterol, more or less ionic surface active substances such as dicetylphosphate, stearylamine or phosphatidic acid, and/or other materials of a hydrophobic nature.

The diameters of the liposomes generally range from 15 nm to $5\mu$.

The preparation or process generally carried out according to the known art comprises two main steps: The preparation of the liposomes and the purification of same from non-entrapped drug.

(1) Preparation of the liposomes: the lipidic or lipophilic components are dissolved in a suitable solvent which is then evaporated to dryness, generally under vacuum.

The aqueous layer containing the drug is added to the flask containing the residue as a thin layer and the whole is submitted to mechanical or ultrasonic shaking for a time ranging from 10 seconds to several hours. The nonhomogeneous layer so obtained (generally indicated as a liposomic suspension), must be purified from the non-entrapped drug.

(2) Separation of the liposomes from the non-entrapped drug: this procedure is usually carried out by elution on a chromatographic column using resins having an exclusively molecular sieve-function, such as Sepharose ®, 2B, 4B or 6B, or the like.

Liposomes are first recovered, while the free drug is retained by the resin.

Another method is ultracentrifugation at 100,000 g and subsequent washing, always by ultracentrifugation with a buffered solution. Still another method also used is dialysis.

The present invention relates to a new purification process for the non-homogeneous layer known as liposomic suspension by both liquid and solid polymers which generally are of synthetic or organic nature with chemical functionality which can be used as ion-exchangers, such as for example, those based on styrene, divinylbenzene, acrylic or methacrylic acid, and usually known as ion-exchange resins. These ion-exchange resins may contain anionic or cationic functions (depending on the drug to be removed) in a matrix which may be a phenolformaldehyde polymer, a styrene-divinylbenzene copolymer, an acrylate or methacrylate polymer, a hydrocarbon polymer or a condensation resin. The anionic functions may be primary, secondary or tertiary aminic or phosphinic functions, or quaternary ammonium ions. The cationic functions may be carboxylic, phosphonic and sulfonic acid cations.

A predetermined quantity of one or more of the resins above reported is introduced directly into the flask containing the liposomic suspension to be purified and this is submitted to shaking for 10 to 60 minutes. After filtration through a sintered glass filter able to retain the ion-exchange resin on which the non-entrapped drug has been adsorbed, the liposomic pure suspension is obtained, which then may be submitted to lyophilization.

This purification procedure of the liposomic suspensions with ion-exchange resins shows the great advantage of maintaining highly concentrated liposomic suspensions (up to 5 mg/ml of doxorubicin HCl) which cannot be maintained by chromatography on a molecular sieve column (max 0.3 mg/ml). The liposomic suspension so obtained is very stable and is not inclined to sediment or settle-out, unlike those obtained by ultracentrifugation.

The same result is achieved by employing, instead of ion-exchange resins, polymers and copolymers with no specific chemical function and which normally, but not exclusively, react according to Van der Waals' forces, generally known as adsorbent resins. These resins can be employed in the purification of liposomic suspensions owing to the difference of polarity between the hydrophobic substances forming the liposomic shell and the drugs of more or less hydrophilic nature.

The final chemical stabilization is achieved by lyophilization of the liposomic suspension.

The following examples are given for illustrative purposes in order still better to demonstrate the invention and its advantages:

EXAMPLE 1

In a saponification flask the following quantities of lipids were dissolved in chloroform and evaporated under vacuum to dryness: 1.5 g of egg lecithin, 0.4 g of cholesterol, and 0.2 g of dicetylphosphate.

A solution of doxorubicin hydrochloride (at a concentration of 10 mg/ml) was poured into the flask, in buffer phosphate 0.007N, and the suspension subjected to ultrasonic shaking for 1 minute.

The suspension was allowed to stand for 30 minutes at room temperature under nitrogen. 2 g of a resin, previously activated in sodium form, obtained by polymerization of methylmethacrylate properly "cross-linked" with a chemical reagent, such as divinylbenzene, with carboxylic functionality and macroreticular structure, which allows its use also in hydrophobic solutions, commercially known by the trademark IRC-50 and produced by Rohm and Haas, were then added (weight refers to dry weight and is equivalent to 5 ml of inflated or swollen resin).

The flask was subjected for about 30 minutes to shaking and then the suspension was filtered through a G 1 porous sheet of filter paper.

Liposomes of size varying from 0.5 to $2\mu$ and containing about 60% of the starting amount of doxorubicin so obtained were stabilized by lyophilization.

EXAMPLE 2

Operating as previously described in Example 1, and with the same amounts of lipids and doxorubicin, the ultra-sonic shaking time was extended to 10 minutes in order to obtain liposomes of size less than $1\mu$.

Since the liposomes were not perfectly homogeneous in size, a non-granular resin was used having also a sieve function. 10 ml of resin of the type known on the market as DOWEX 50-X 4 100–200 Mesh (trademark) previously activated in sodium form were therefore added.

After filtration, a suspension was obtained containing liposomes of size varying from 0.2 to $0.8\mu$ and comprising 75% of the starting doxocrubicin.

The liposomes were stabilized by lyophilization.

EXAMPLE 3

A solution of 5-fluorouracil at a concentration of 10 mg/ml in buffer phosphate 0.007N at pH 8 was poured into a saponification flask containing the lipidic phase prepared as above described.

The suspension was treated as in Example 1, using as filtering resin 10 ml of the type known on the market as Amberlite IRA-400 (Cl) previously activated as the hydrochloride.

The liposomes so obtained were stabilized by lyophilization.

EXAMPLE 4

The liposomes of 5-fluorouracil were prepared operating as previously described with the following amounts of lipids: 1.5 g of egg lecithin, 0.4 g of cholesterol, and 0.2 g of stearylamine.

As purification system, 10 ml of a resin of the type known on the market as DOWEX 1 (50–100 Mesh), previously activated, were employed.

The liposomes so obtained were stabilized by lyophilization.

EXAMPLE 5

Example 2 was repeated, except that the resin DOWEX 50W-X, 100–200 Mesh, was replaced by 15 g of adsorbent resin Rohm and Haas XAD 7, and the shaking time was extended to 40 minutes.

After filtration through sintered filter glass G 1, a suspension of liposomes containing about 50% of the starting amount of doxorubicin was obtained.

The liposomes were stabilized by lyophilization.

EXAMPLE 6

1.5 g of soya-lecithin, 0.4 g of cholesterol, and 0.3 g of dicetylphosphate were dissolved in $CH_2Cl_2$ and to this solution another solution of aminosidine sulphate in 0.02M buffer phosphate at pH 6.5 at the concentration of 3 mg/ml was added.

The two phases were emulsified and as an emulsion subjected to shaking, and nitrogen was bubbled in at room temperature until the complete removal of the methylene chloride took place.

The suspension was stabilized at room temperature for 4 hours, then into the flask was poured an amount of resin, known commercially by the trademark "IRC-50 or Rohm and Haas," equivalent to 5 g of dry resin.

After 1 hour of shaking, the liposomic suspension was filtered on a sintered glass filter to remove the resin which had retained the non-entrapped drug.

The liposomic suspension was then stabilized by lyophilization.

EXAMPLE 7

Operating as previously described in Example 6, 2.3 g of lecithin ex-egg, 0.65 g of cholesterol and 0.15 g of octadecylamine have been dissolved in 50 ml of $Ch_2Cl_2$ and the solution had been poured into a flask containing 250 mg of m-benzoylhydratropic acid (generic name Ketoprofen) in 150 ml of Na,K buffer phosphate 0,02M at pH 7.4.

Inert gas ($N_2$) has been poured into the flask kept under shaking till complete removal of the organic solvent and the resulting formation of liposomic suspension, to which 10 ml of anion exchange resin IRA 400 ($Cl^-$) manufactured by Rohm and Haas have been added.

After 30 minutes of shaking, the resin has been removed by filtration and the purified liposomic suspension has been lyophilized.

What is claimed is:

1. A method for removing a non-entrapped drug from a liposomic suspension, comprising:
    (a) contacting said suspension with an ion-exchange resin capable of selectively binding said non-entrapped drug by mixing said suspension with said resin; and
    (b) separating said resin-bound drug from said suspension by passing said mixture through a filter medium capable of retaining said resin and filtrating said suspension.

2. The method of claim 1 wherein said resin is selected from the group consisting of polymers of phenolformaldehyde, copolymers of styrene-divinylbenzene, acrylates and methacrylates.

3. The method of claim 1 wherein said ion-exchange resin is a liquid polymer based on at least one monomer selected from the group consisting of styrene, divinylbenzene, acrylic acid, and methacrylic acid.

4. The method of claim 1 wherein said ion-exchange resin is a solid polymer based on at least one monomer selected from the group consisting of styrene, divinylbenzene, acrylic acid, and methacrylic acid.

5. The method according to claim 3 or 4 wherein said ion-exchange resin is selected from the group consisting of weak strength, average strength, and strong strength cationic-type resins, said resins comprising functions selected from the group consisting of carboxylic, phosphonic, and sulfonic acids.

6. The method of claim 1 wherein said resin is selected from the group consisting of hydrocarbon resins, and condensation resins.

7. A method according to claim 1 wherein said ion-exchange resin is selected from the group consisting of weak strength and average strength anionic first and second type resins, said resins comprising functions selected from the group consisting of quaternary ammonium ions, primary, secondary and tertiary aminic and phosphinic functions appended to matrices selected from the group consisting of phenolformaldehyde, styrene-divinylbenzene, acrylates, and methacrylates.

8. The method of claim 7, wherein said matrices are selected from the group consisting of hydrocarbon and condensation resins.

9. A method according to claim 1 wherein said ion-exchange resin is in salified or activated form.

10. A method for removing a non-entrapped drug from a liposomic suspension, comprising:
    (a) contacting said suspension with an adsorbent material capable of selectively adsorbing said non-entrapped drug in a nonionic chemical manner at least partially based on Van der Waals forces, by mixing said suspension with said adsorbent substance; and (b) separating said adsorbent-bound drug from said suspension by passing said mixture through a filter medium capable of retaining said adsorbent material and filtrating said suspension.

11. A method according to claim 10 wherein said adsorbent material is selected from the group consisting of aliphatic resins and aromatic resins having adsorbent properties at least partially due to Van der Waals forces.

12. The method of claim 1 or 11 further comprising a step:

(c) stabilizing said filtrate by lyophilization.

* * * * *

UNITED STATES PATENT AND TRADEMARK OFFICE
CERTIFICATE OF CORRECTION

PATENT NO.  : 4,460,577
DATED       : July 17, 1984
INVENTOR(S) : MORO, et al.

It is certified that error appears in the above-identified patent and that said Letters Patent is hereby corrected as shown below:

Column 1, line 27, for "sphingomycelin" read --sphingomyelin--

Column 2, line 65, for "filter paper" read --filter material--

Signed and Sealed this

Twenty-sixth Day of February 1985

[SEAL]

Attest:

DONALD J. QUIGG

Attesting Officer

Acting Commissioner of Patents and Trademarks